United States Patent

Bernt et al.

[11] 3,986,931
[45] Oct. 19, 1976

[54] γ-GLUTAMYL-4-NITROANILIDE COMPOUNDS AND THEIR USE IN DETERMINING γ-GLUTAMYL TRANSPEPTIDASE

[75] Inventors: Erich Bernt, Munich; Wolfgang Gruber, Garatshausen; Erich Haid; Fritz Stähler, both of Tutzing; August Wilhelm Wahlefeld, Weilheim; Günter Weimann, Tutzing, all of Germany

[73] Assignee: Boehringer Mannheim G.m.b.H., Mannheim, Germany

[22] Filed: Aug. 4, 1975

[21] Appl. No.: 601,775

Related U.S. Application Data

[62] Division of Ser. No. 419,455, Nov. 27, 1973.

[30] Foreign Application Priority Data

Dec. 5, 1972 Germany.............................. 2259512
July 3, 1973 Germany.............................. 2333798

[52] U.S. Cl............................................. 195/103.5 R
[51] Int. Cl.²......................................... C12K 1/04
[58] Field of Search........... 195/103.5 R; 260/518 R

[56] References Cited
UNITED STATES PATENTS 3,703,441 11/1972 Nakanishi et al............ 195/103.5 R
3,773,626 11/1973 Bernt et al.................. 195/103.5 R
3,892,631 7/1975 Carroll....................... 195/103.5 R

*Primary Examiner*—A. Louis Monacell
*Assistant Examiner*—C. A. Fan
*Attorney, Agent, or Firm*—Burgess, Dinklage & Sprung

[57] ABSTRACT

γ-Glutamyl-4-nitroanilide compounds of the formula

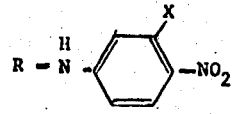

wherein R is a γ-glutamyl radical and X is an acid group, and salts of such compounds, are used to determine γ-glutamyltranspeptidase by contacting a sample suspected of containing γ-glutamyltranspeptidase with said compound and glycyl-glycine and determining the liberation of the resulting p-nitroaniline compound as a measure of the γ-glutamyltranspeptidase activity initially present in the sample.

13 Claims, No Drawings

Γ-GLUTAMYL-4-NITROANILIDE COMPOUNDS AND THEIR USE IN DETERMINING Γ-GLUTAMYL TRANSPEPTIDASE

This is a division of application Ser. No. 419,455, filed Nov. 27, 1973

This invention relates to novel γ-glutamyl-4-nitroanilide compounds, to compositions containing them, and to their use in determining the activity of γ-glutamyl-transpeptidase.

γ-Glutamyltranspeptidase (γ-GT) determinations are performed increasingly in the clinical laboratory for the diagnosis of liver diseases. In accordance with a known method, this determination is performed on the basis of the reaction:

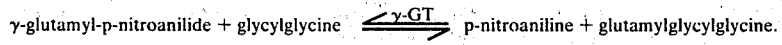

γ-glutamyl-p-nitroanilide + glycylglycine ⇌ (γ-GT) p-nitroaniline + glutamylglycylglycine.

The speed with which the yellow-colored p-nitroaniline is liberated can be determined optically and is a measure of the γ-GT activity that is present.

The instability and poor solubility of the substrate γ-glutamyl-p-nitroanilide is, however, a severe disadvantage as regards the routine application of this method. It is difficult to dissolve the compound, and after it is dissolved, the solutions remain usable for only a short time (approximately 2 hours). It has therefore been necessary to prepare solutions large enough to perform relatively few determinations which have to be performed very soon. Another disadvantage has been that the substance has had to be dissolved at 50° to 60° C, but if this temperature is exceeded, the substance hydrolyzes spontaneously. Such hydrolysis has a great effect on the optical extinction of the solutions, which is essential to the masurement. This is particularly disadvantageous when the γ-GT determination is performed in automatic analyzers because, due to the high absorption thus produced, the greater activities cannot be measured with sufficient precision. Consequently, the measurement has hitherto been performed at suboptimal substrate concentrations of only 3 to 4 mM in contrast to the optimum concentration at about 6 mM (Clin. Chim. Acta 31 (1971), 175–179).

The disadvantages described have been partially remedied by the reagent described in German "Auslegeschrift" No. 2,042,829 in which the procedure is executed in the presence of a surface-active substance and of polyvinylpyrrolidone. With this reagent the solubility characteristics of γ-glutamyl-p-nitroanilide can be greatly improved and the useful life of the solutions is substantially increased. In this case, too, however, heating at 50° to 60° C is necessary, with the danger of spontaneous hydrolysis and the inaccuracy of measurement which is caused thereby.

There therefore has been a need for compounds which, on the one hand, will have substantially better solubility characteristics than γ-glutamyl-p-nitroanilide, but which, on the other hand, will be equally good substrates for the γ-GT enzyme.

The instant invention provides such materials.

The compounds of the invention are γ-glutamyl-4-nitroanilide compounds of the formula

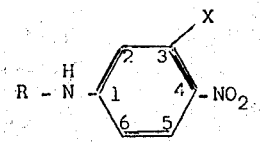

in which R represents the γ-glutamyl radical,

and X represents an acid group.

The compounds of the invention are thus characterized by an acid group in position 3 of the nitroaniline. Examples of suitable acid groups are the carboxyl group and its homologs such as the acetyl group etc., of, e.g., up to 6 carbon atoms, the thioanalogs thereto, sulfonyl groups, thiosulfonyl groups, phosphatyl groups, sulfhydryl groups, and the like. The carboxyl and the sulfonyl groups are preferred.

Positions 2, 5 and 6 of the compounds of the invention are preferably unsubstituted. However, one or more low alkyl groups having 1 to 3 carbon atoms may also be present. The compouns can of course, be used in their salt form, e.g., their ammonium, alkali metal, alkaline earth metal or amino salt forms.

The compounds of the invention substantially eliminate the above-mentioned disadvantages of γ-glutamyl-p-nitroanilide; on the one hand, they have excellent solubility characteristics and on the other hand, they are very good substrates for the γ-GT enzyme. The latter fact is especially surprising, because most of the derivatives of γ-glutamyl-p-nitroanilide having solubility-improving substituents cannot serve as a substrate for γ-GT. This is shown by the experimental findings made with a great number of derivatives of γ-glutamyl-p-nitroanilide which are summarized in the following table.

The table shows that only the compounds of the invention combine improved solubility with good characteristics as a substrate for γ-GT.

Where no meaning is given in the table for X, A, B or C, they represent hydrogen.

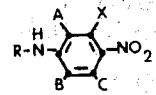

| | | Conversion based on GLUPA* | Concentration in the test | Solubility | Melting point | Thin layer chromatography | Electrophoretic mobility |
|---|---|---|---|---|---|---|---|
| 1. | X = COONH₄ | 115 % | 10 mM | ≧300 mM | 185–187° C | 0.94 | 0.81 |
| 2. | X = SO₃NH₄ | 160 % | 8 mM | ≧300 mM | 186–187° C | 0.79 | 0.82 |

-continued

| R-N(A,B,C,X)-NO2 | | Conversion based on GLUPA* | Concentration in the test | Solubility | Melting point | Thin layer chromatography | Electrophoretic mobility |
|---|---|---|---|---|---|---|---|
| 3. | X = COONH$_4$ | 30–40 % | 4 mM | | | 1.65 | 0.725 |
|  | C = CH$_3$ | 20–30 % | 8 mM | | | | |
| 4. | A = COONH$_4$ | 0 | to 8 mM | >120 mM | 176° C free acid | 1.5 free acid | 0.72 free acid |
| 5. | A = SO$_3$NH$_4$ | 0 | to 8 mM | >120 mM | | | |
| 6. | A = OH | 0 at 546 nm | to 4 mM | <4 mM | 217–219° C | 1.75 | 0.68 |
| 7. | A = CH$_3$ | about 45 % | 4 mM | <60 mM | 180° C | 1.68 | 0.265 |
| 8. | X = CONH$_2$ | 15 % | 8 mM | 8 mM | 216° C | 1.27 | 0.26 |
| 9. | X = Cl | 25 % | <4 mM | <4 mM | | 2.1 | 0.26 |
| 10. | X = OH | Initial extinction too high not measurable | | | 185–187° C | 1.9 | 0.69 |
| 11. | X = OCH$_3$ | 15–25 % | 4 mM | | | 1.79 | 0.23 |
| 12. | X = Morpholino | 10 % | 2 mM | No greater amount can be used on account of inherent coloring | | 1.51 | 0.197 |
| 13. | A = Cl | Turbid cannot be evaluated | 4 mM | 4 mM | not measurable | 1.57 | 0.25 |
| 14. | X = C = COONH$_4$ | 22.3 % | 4 mM | | | | |
| 15. | X = —O—CH$_2$—COONH$_4$ | 21.5 % at 436 nm | 4 mM | 4 mM | | | |
| 16. | R-NH-(C$_6$H$_3$)(NO$_2$)-NH$_2$ | 3 % | about 1 mM | about 1 mM | 208° C | 1.45 | 0.20 |
| 17. | R-NH-(C$_6$H$_4$)-NO$_2$ | about 3 % | 4 mM | 4 mM | | 1.48 | 0.22 |
| 18. | R-NH-(pyridyl)-NO$_2$ | 20 % | 4 mM | 4 mM | 178–180° C | 1.48 | 0.23 |

*GLUPA γ-glutamyl-p-nitroaniline

The melting points were determined according to Kofler. The thin-layer chromatography was performed on silica gel with a mixture of n-butanol, glacial acetic acid and water in a ratio of 50 : 15 : 25. The values given refer to glutamic acid = 1.0 (Rf = 0.32 − 0.33).

The electrophoretic mobility was determined in triethylammonium bicarbonate buffer 0.05 M, pH 7.5, and refers to glutamic acid = 1.0.

The compounds of the above table are all new. They were prepared by the reaction of an activated glutamic acid, bearing an amino group protected in a conventional manner, with a p-nitroaniline derivative bearing the substituents given in the table, followed by cleavage of the protective group from the glutamic acid-p-nitroanilide derivative that had been formed. Wherever compounds in accordance with the invention are formed, a p-nitroaniline bearing an acid group in position 3 was used, preferably a 3-carboxy- or 3-sulfo-p-nitroaniline.

The activated glutamic acid used should preferably be the corresponding anhydride or a halide, preferably a chloride or bromide. The anhydride may be obtained, for example, by reacting glutamic acid, after introducing a protective group, with acetic acid anhydride to produce the corresponding glutamic acid anhydride. Examples of suitable protective groups are phthaloyl-benzyl-carbobenzoxy-f-butyloxycarbonyl-group, etc.

The removal of the protective group may also be performed by known methods. Cleavage with hydrazine is preferred if a phthaloyl group is present.

Instead of glutamic acid anhydride or halide, any other activated glutamic acid derivative may be used which is capable of facilitating the creation of the acid amide bond between the carboxyl group of the glutamic acid and the amino group of the aniline. Activated derivatives of this kind are known from peptide chemistry.

If the preferred reaction using phthaloylglutamic acid anhydride or halide is selected, it is best conducted in an organic solvent, in the presence of an amine if desired. Dioxane is preferred as the organic solvent, although other solvents may also be used, such as tetrahydrofuran, dimethylformamide, and the like. A tertiary aliphatic amine is preferred as the amine, especially one having 1 to 6 carbon atoms per alkyl group. The reaction with hydrazine can best take place in a low alcohol as solvent.

For the refinement of the crude products conventional methods are used, such as recrystallization or chromatography, e.g., anion exchange chromatography and/or adsorption chromatography using such adsorbers as silica gel, aluminum hydroxide and the like, such as are suitable especially for thin-layer chromatography, or the recrystallization of the ammonium salts from a water-acetone mixture.

The compounds of the invention are easily soluble at room temperature and achieve more than 100% of the reaction rate of γ-glutamyl-p-nitroanilide under the same conditions. The compounds of the invention are therefore superior substrates for the determination of γ-glutamyltranspeptidase.

The solubility of the preferred compounds of the invention even without solubilizer is more than/300/mM, that is, it is at least a hundred times greater than the solubility of γ-glutamyl-p-nitroanilide.

The following examples illustrates the preparation of the compounds of the invention, their properties and their use as substrates for the determination of γ-glutamyltranspeptidase (γ-GT).

The compounds of the invention not only have a better solubility than γ-glutamyl-p-nitroanilide, but also they require no heating to dissolve them, so that excessively high blind extinctions are avoided. Stability in solution is good; in the optimization of test conditions for the determination of γ-GT no problems are encountered, and this is of great importance for the requirements of clinical chemistry. The preparation of the compounds is easy and inexpensive; the sensitivity of the measuring set-up is the same as it is when γ-glutamyl-p-nitroanilide is used.

EXAMPLE 1

Preparation of γ-glutamyl-p-nitroanilide-3-carboxylic acid (GLUPA-3-carboxylic acid)

9.1 g of 2-nitro-5-aminobenzoic acid (50 millimoles) and 14.2 g of phthaloylglutamic acid anhydride (55 millimoles) were dissolved in 50 ml of absolute dioxane after the addition of 13 ml of tributyl amine. The reaction mixture was refluxed for two hours. After cooling, 100 ml of 2N ammonia was added to the reaction mixture and the tributylamine that separated was extracted with ether. The aqueous solution was concentrated until dry, dissolved in methanol, and adjusted to pH 10 with 80% hydrazine hydrate. The reaction solution was let stand at room temperature for about twenty hours, during which time a product partially separated which, after filtration and washing with methanol, was discarded. The methanolic filtrate was concentrated until dry and the residual oil was dissolved in about 300 ml of distilled water.

This aqueous solution was chromatographed on a column containing 100 ml of Dowex 1 X 2 (50–100 mesh) Formiat-Form, washed with 300 ml distilled water and eluted, graduating with 2 liters of water against 2 liters of 0.5N ammonium carbonate solution. The eluate was collected in 100 ml fractions and tested by thin-layer chromatography (silica gel plates made by Riedel de Haen, No. 37350) in a mixture of butanol, glacial acetic acid and water is a ratio of 50:15:15 (chromatogram development: blue spots in ultraviolet light, or, after spraying with ninhydrin followed by heating, brown spots in the zones containing amino acid). The fractions containing the product glutamic acid-P-nitroanilide-3-carboxylic acid ($R_f$ value 0.25) were collected and concentrated in vacuo until dry. The remaining powder is biturated with abs ethanol, filtered and dried in vacuo over calcium chloride.

Yield: 7 g γ-glutamyl-p-nitroanilide-3-carboxylic acid, momoammonium salt (58% of theory); Ultraviolet spectrum: λ max = 317 nm, ε = 11.7 [cm²/μmole] at 317 nm.

EXAMPLE 2

The use of GLUPA-3-carboxylic acid for determination of γ-GT

2-Nitro-5-aminobenzoic acid was liberated during the enzymatic cleavage. Its ultraviolet spectrum had the following characteristics:

λ max = 380 nm
ε = 9.4 [cm²/μmole] at 405 nm = 12.75 [cm²/μmole] at 380 nm;
= 9.83 × 10⁻⁵ M.

A. Performance of the Measurement

Pipette the following into a cell:

| | |
|---|---|
| 0.1 M tris-buffer, 100mM glycylglycine, pH = 8.25 | 2.8 ml |
| 130 mM GLUPA-3-carboxylic acid in above buffer | 0.2 ml |
| Adjust temperature to 25° C. Begin determination by adding: | |
| Human serum | 0.2 ml |

Stir, read extinction at 405 nm and simultaneously start the stopwatch. Read again after precisely one, two and three minutes.

Determine the average of the extinction differences per minute (Δ E/min) and use in the computation.

B. Computation

One international unit (U) is the enzyme activity which will react 1 μmole of substrate in one minute at 25° C. The bais is to be 1 ml of body fluid, e.g., serum. For the computation of the enzyme activity per milliliter (A), the following formula generally applies:

$$A = \frac{V \cdot 1000}{\min \cdot \epsilon \cdot d \cdot v} \Delta E \text{ (mU/ml)}$$

The extinction coefficient (ε) of 3-carboxy-4-nitroaniline amounts to 9.4 cm²/μmole at 405 nm. The layer thickness (d) of the cell is 1 cm, v is the volume of the serum used (0.2 ml), V is the total of the volumes (3.2 ml). The measurement of the extinction E is performed at intervals of one minute. Consequently, $$A = \Delta E \text{ (405 nm) / min} \times 1702 \text{ (mU/ml)}.$$

EXAMPLE 3

Preparation of γ-glutamyl-4-nitroanilide-3-sulfonic acid (gluta-3 sulfonic acid)

115 g of aniline-4-nitro-3-sulfonic acid and 150 g of phthaloylglutamic acid anhydride were suspended in 2 liters of absolute dimethylformamide and then heated in the oil bath to 145° C.

After this temperature was reached the mixture was kept at 145° C for one hour and then cooled. The mixture was filtered and the filtrate concentrated in vacuo until dry. The oily residue was dissolved in methanol and adjusted with 80% hydrazine hydroxide to pH 9. After 24 hours the crystals formed were removed by suction filter, washed with a small amount of methanol and discarded.

The filtrate was concentrated until dry and intensely cooled acetone was cautiously added, with cooling. The precipitate that formed was suction filtered, washed well with acetone, and the residue dissolved in water with stirring. The water-insoluble residue was filtered off and the filtrate was adjusted with ammonia to pH 7.5 and concentrated. The ammonium salt of γ-glutamyl-4-nitroanilide-3-sulfonic acid was crystallized out by the addition of acetone. The product crystallized very well in light-yellow druses.

Melting Point: 186°–187° C.

Spectrum showed absorption maximum at 290 nm = 4.57 [cm$^2$/μmole]

Yield: Approximately 115–120 g; another 15 to 20 g may be obtained from the crystallization mother liquor.

Total yield approx. 135 g, corresponding to 70% of the theory.

The compound is easily soluble at room temperature and achieves about 160% of the reaction rate of γ-glutamyl-p-nitroanilide under the same conditions.

EXAMPLE 4

Use of GLUPA-3-sulfonic acid for determination of γ-GT

In the enzymatic cleavage of the compound of the invention p-nitroaniline-3-sulfonic acid is liberated. Its ultraviolet spectrum has the following characteristics:

λ max = 380 nm
ε = 5.45 [cm$^2$/μmole] at 405 nm = 7.38 [cm$^2$/μmole] at 380 nm.

A. Performance of the Measurement

Pipette the following into a cell:

| | |
|---|---|
| 0.1 m tris-buffer, 150 mM glycylglycine, pH = 8.5 | 2.8 ml. |
| 130 mM GLUPA-3-sulfonic acid in above buffer | 0.2 ml |
| Adjust temperature to 25° C. Begin determination by the addition of | |
| Human serum | 0.2 ml |

Stir, read extinction at 405 nm, and at the same time start the stop watch. Repeat the reading after precisely one, two and three minutes.

Compute the average of the extinction differences per minute (Δ E/min) and use this in the computation.

B. Computation

One international unit (U) is the enzyme activity which reacts 1 μmole of substrate in one minute at 25° C. The basis is 1 ml of body fluid such as serum. For the computation of the enzyme activities per ml (A) the following formula generally applies:

$$A = \frac{V \cdot 1000}{min \cdot \epsilon \cdot d \cdot v} \Delta E \text{ (mU/ml)}$$

The extinction coefficient (ε) of p-nitroaniline-3-sulfonic acid amounts to 5.45 cm$^2$/μM at 405 nm under the test conditions. The layer thickness (d) of the cell is 1 cm, v is the volume of the serum used (0.2 ml), V is the sum of the volumes (3.2 ml). The measurement of the extinction E is performed at intervals of one minute. The result is:

$$A = \Delta E \text{ (405 nm) / min} \times 2936 \text{ (mU/ml)}.$$

It will be understood that the foregoing specification and examples are illustrative but not limitative of the present invention inasmuch as other embodiments within the spirit and scope of the invention will suggest themselves to those skilled in the art.

What is claimed is:

1. Method of determining the γ-glutamyltranspeptidase of a content of a sample suspected of containing same, which method comprises contacting such sample with a γ-glutamyl-4-nitroanilide compound of the formula

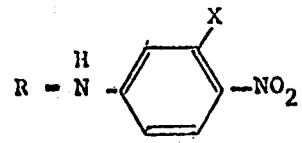

wherein
R is a γ-glutamyl radical and
X is a carboxyl group or homologs thereof containing up to 6 carbon atoms, a sulfonic acid group, a thiosulfonyl group, a sulfhydryl group, or a phosphatyl group; and alkali, alkaline earth, ammonium and amine salts thereof and
a glycylglycine and measuring the liberation of the corresponding p-nitroaniline compound as a measure of the γ-glutamyltranspeptidase activity initially present in the sample.

2. Method as claimed in claim 1, wherein said liberation of the p-nitroaniline compound is measured optically.

3. Method as claimed in claim 1, wherein said γ-glutamyl-3-nitroanilide compound is in its ammonium, alkali metal, alkaline earth metal, or amine salt form.

4. Method as claimed in claim 1 wherein X in the formula is a carboxyl group.

5. Method as claimed in claim 1 wherein X in the formula is a sulfonic acid group.

6. Method as claimed in claim 1 wherein X in the formula is carboxyl-alkyline group of up to 6 carbon atoms.

7. Method as claimed in claim 1 wherein X in the formula is an acetyl group.

8. Method as claimed in claim 1 wherein X in the formula is a thiosulfonyl or sulfhydryl group.

9. Method as claimed in claim 1 wherein X in the formula is a phosphatyl group.

10. Method as claimed in claim 1 wherein said compound is in its ammonium salt form.

11. Method as claimed in claim 1 wherein said compound is in its alkali metal salt form.

12. Method as claimed in claim 1 wherein said compound is in its alkaline earth metal salt form.

13. Method as claimed in claim 1 wherein said compound is in its amine salt form.

* * * * *